(12) United States Patent
Prakash et al.

(10) Patent No.: US 11,620,506 B2
(45) Date of Patent: Apr. 4, 2023

(54) CONDENSED MEMORY NETWORKS

(71) Applicant: KONINKLIJKE PHILIPS N.V., Eindhoven (NL)

(72) Inventors: Aaditya Prakash, Cambridge, MA (US); Sheikh Sadid AL Hasan, Cambridge, MA (US); Oladimeji Feyisetan Farri, Yorktown Heights, NY (US); Kathy Mi Young Lee, Westford, MA (US); Vivek Varma Datla, Watertown, MA (US); Ashequl Qadir, Melrose, MA (US); Junyi Liu, Revere, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1054 days.

(21) Appl. No.: 15/707,550

(22) Filed: Sep. 18, 2017

(65) Prior Publication Data
US 2019/0087721 A1 Mar. 21, 2019

(51) Int. Cl.
*G06N 3/08* (2006.01)
*G06N 3/04* (2006.01)
*G16H 50/20* (2018.01)

(52) U.S. Cl.
CPC .............. *G06N 3/08* (2013.01); *G06N 3/0427* (2013.01); *G06N 3/0445* (2013.01); *G16H 50/20* (2018.01)

(58) Field of Classification Search
CPC ....... G06N 3/08; G06N 3/0445; G06N 3/0427
See application file for complete search history.

(56) References Cited

U.S. PATENT DOCUMENTS

| | | | | |
|---|---|---|---|---|
| 2017/0076196 | A1* | 3/2017 | Sainath | G06N 3/084 |
| 2017/0293725 | A1* | 10/2017 | Liu | G06F 40/30 |
| 2018/0174043 | A1* | 6/2018 | Po | G06N 3/08 |
| 2019/0034591 | A1* | 1/2019 | Mossin | G16H 10/60 |
| 2019/0043486 | A1* | 2/2019 | Salloum | G10L 15/16 |

OTHER PUBLICATIONS

Kapashi et al, Answering Reading Comprehension Using Memory Networks (Year: 2015).*
Miller et al, Key-Value Memory Networks for Directly Reading Documents (Year: 2016).*
Nguyen et al, Deepr: A Convolutional Net for Medical Records (Year: 2017).*

(Continued)

*Primary Examiner* — Abdullah Al Kawsar
*Assistant Examiner* — Tewodros E Mengistu

(57) ABSTRACT

Techniques are described herein for training and applying memory neural networks, such as "condensed" memory neural networks ("C-MemNN") and/or "average" memory neural networks ("A-MemNN"). In various embodiments, the memory neural networks may be iteratively trained using training data in the form of free form clinical notes and clinical reference documents. In various embodiments, during each iteration of the training, a so-called "condensed" memory state may be generated and used as part of the next iteration. Once trained, a free form clinical note associated with a patient may be applied as input across the memory neural network to predict one or more diagnoses or outcomes of the patient.

17 Claims, 5 Drawing Sheets

(56) References Cited

OTHER PUBLICATIONS

Prakash et al, Condensed Memory Networks for Clinical Diagnostic Inference (Year: 2016).*
Luo, Recurrent neural networks for classifying relations in clinical notes, Jul. 8, 2017 (Year: 2017).*
Abdi, Quality Assessment of Echocardiographic Cine Using Recurrent Neural Networks: Feasibility on Five Standard View Planes, Sep. 4, 2017 (Year: 2017).*
Dernoncourt, De-identification of Patient Notes with Recurrent Neural Networks (Year: 2016).*
Huang, Bidirectional LSTM-CRF Models for Sequence Tagging (Year: 2015).*
Xiong, et al., "Dynamic Memory Networks for Visual and Textual Question Answering", Proceedings of the 33rd International Conference on Machine Learning, New York, NY, USA, 2016. JMLR: W&CP vol. 48.
Evangelopoulos, "Efficient Hardware Mapping of Long Short-Term Memory Neural Networks for Automatic Speech Recognition", Thesis submitted for the degree of Master of Science, Academic Year 2015-2016, 131 pages.
Cheng, et al., "Long Short-Term Memory-Networks for Machine Reading", School of Informatics, University of Edinburgh, Sep. 20, 2016 (Abstract).
Prakash, et al., "Condensed Memory Networks for Clinical Diagnostic Inferencing", Association for the Advancement of Artificial Intelligence, Artificial Intelligence Laboratory, Philips Research North America, Cambridge, MA, Jan. 3, 2017 (Abstract).

* cited by examiner

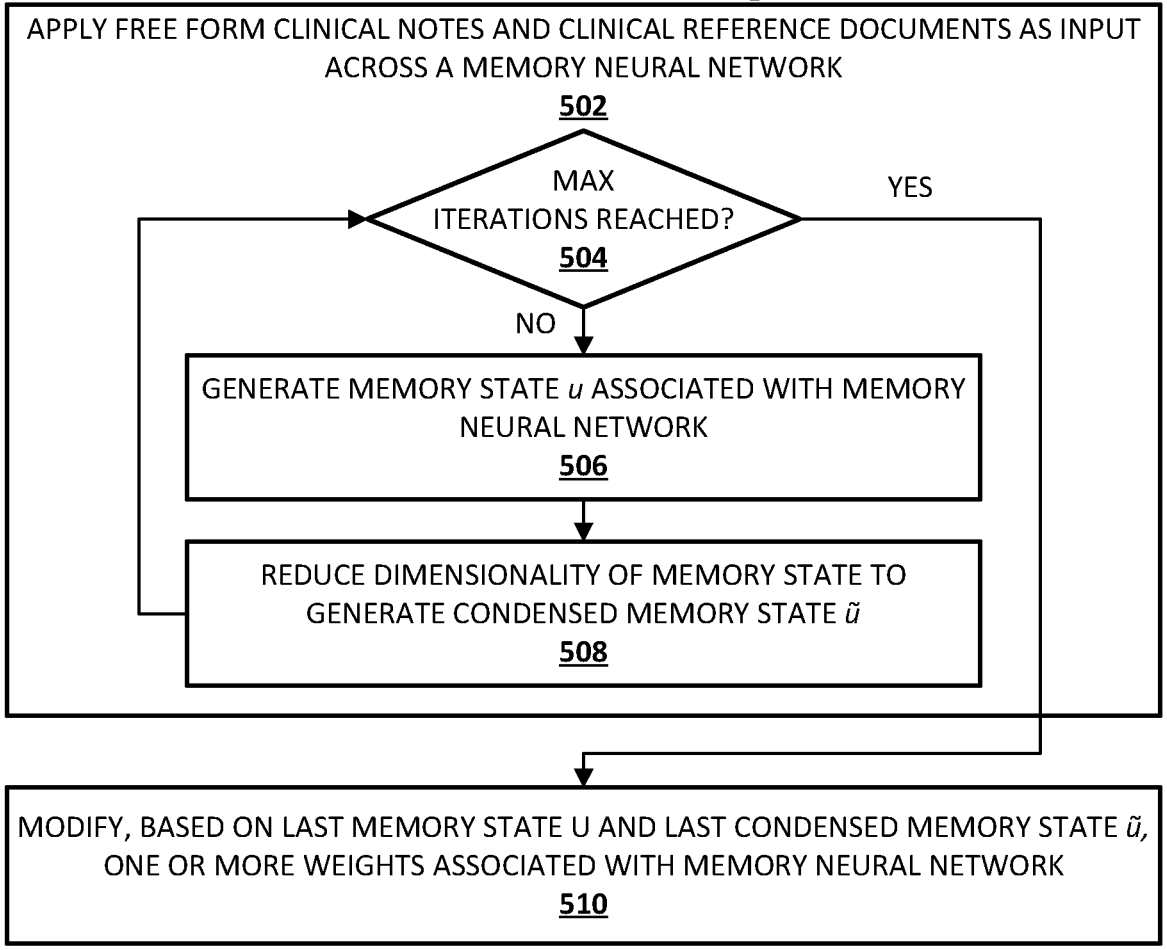
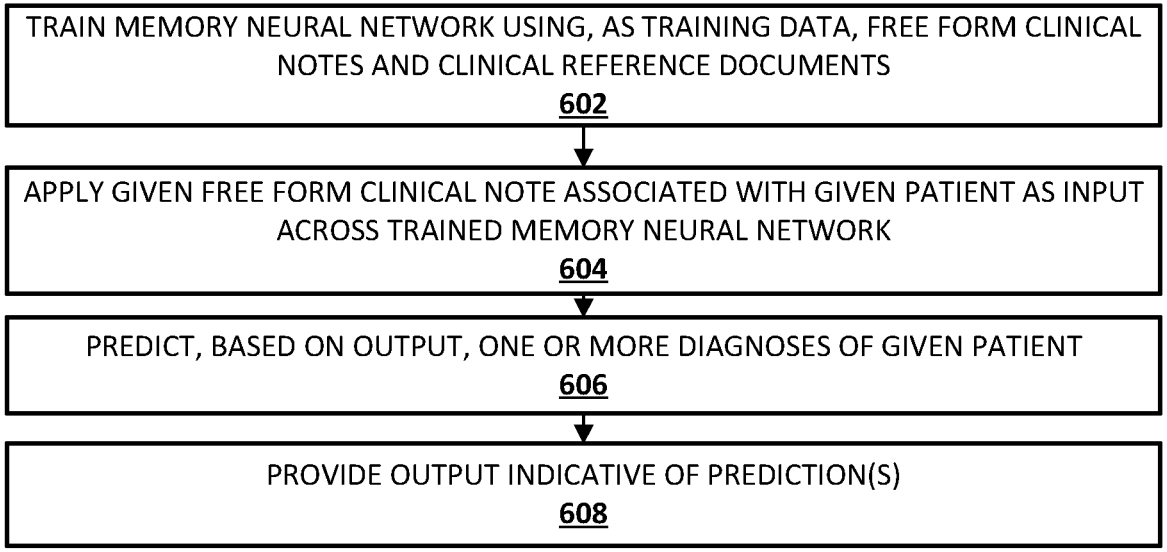

CONDENSED MEMORY NETWORKS

TECHNICAL FIELD

Various embodiments described herein are directed generally to artificial intelligence. More particularly, but not exclusively, various methods and apparatus disclosed herein relate to training and applying condensed memory networks to make predictions.

BACKGROUND

Diagnosis of a clinical condition is a challenging task, which often requires significant medical investigation. Clinicians perform complex cognitive processes to infer the probable diagnosis after observing several variables such as the patient's past medical history, current condition, and various clinical measurements. The cognitive burden of dealing with complex patient situations could be reduced by automatically generating and providing suggestions to physicians of the most probable diagnostic options for optimal clinical decision-making. Previous work related to diagnostic inferencing problems mostly consider multivariate observational data such as physiological signals, lab tests, and so forth. However, these observational data do not tell the full story. In particular, free form clinical notes recorded in, for instance, an electronic health record ("MR"), often may contain pertinent information that is useful to predict diagnoses and/or outcomes.

Memory networks have been demonstrated to be effective in tasks which require comprehension of free-form text. Memory neural networks ("MemNNs") are a class of models which contain an external memory and a controller to read from and write to the memory. MemNNs read a given input source and a knowledge source several times ("hops" or "iterations") while updating an internal memory state associated with the neural network. The memory state is a representation of relevant information from the knowledge base optimized to solve the given task. This allows the MemNN to remember useful features. In particular, a MemNN stores all information (e.g. knowledge base, background context) into a memory that contains a plurality of "slots," assigns a relevance probability to each memory slot using content-based addressing schemes, and reads contents from each memory slot by taking their weighted sum. MemNNs are more difficult to train than traditional neural networks, and do not scale easily to a large memory.

End-to-End Memory Networks and Key-Value Memory Networks ("KV-MemNNs") are attempts to solve these problems by training multiple hops over memory and compartmentalizing memory slots into hashes, respectively. End-to-End Memory Networks do not require strong supervision, unlike MemNNs. However, when memory content becomes large, End-to-End memory networks become difficult to train because they must score all memory content. KV-MemNNs have a key-value paired memory to solve this problem (i.e., by allowing for scoring keys only) and are built upon MemNNs. The key-value paired structure is a generalized way of storing content in the memory. The contents in the key-memory are used to calculate the relevance probabilities whereas the contents in the value-memory are read into the model to help make the final prediction.

Recent attempts have been made to incorporate longer contextual (or "episodic") memory into the basic Recurrent Neural Networks ("RNNs") framework. A "Stack-Augmented RNN" may interconnect RNN modules using a push-down stack in order to learn long-term dependencies. They are able to reproduce complicated sequence patterns. Other techniques employ multi-scale RNNs, which are able to learn a latent hierarchical structure by using temporal representation at different timescales. These methods are well-suited for learning long-term temporal dependencies, but do not scale well to large memory. Hierarchical MemNNs use maximum inner product search ("MIPS") to store memory slots in a hierarchy, but they are difficult to train.

Another related class of models is Attention-based neural networks. These models are trained to learn an attention mechanism so that they can focus on the important information on a given input. Applying an attention mechanism on the machine reading comprehension task has shown promising results. In tasks where inferencing is governed by the input source, e.g., sentence-level machine translation, image caption generation, and/or visual question answering, the use of attention-based models has proven to be very effective. As attention is learned by the iterative finding of the highly-activated input regions, this is not feasible for a large scale external memory.

SUMMARY

The present disclosure is directed to methods and apparatus for training and applying condensed memory networks ("C-MemNNs") and/or average memory neural networks ("A-MemNN") to make various predictions. For example, C-MemNNs take the form of one or more learned models with iterative condensation of memory representations that preserves the hierarchy of features in the memory. Experiments on various datasets such as free form clinical notes show that the condensed memory network models described herein outperform other variants of memory networks to make various predictions, such as the most probable diagnoses given a complex clinical scenario.

Generally, in one aspect, a method for training a memory neural network may include: applying, as training data, a plurality of free form clinical notes and a plurality of clinical reference documents as input across the memory neural network, wherein the applying includes multiple iterations for each instance of the training data, wherein each of the plurality of free form clinical notes includes one or more clinical observations about a patient in textual form, and wherein each clinical reference document describes one or more diagnoses and one or more associated expected clinical observations; for each iteration of the applying: generating a memory state associated with the memory neural network, and reducing a dimensionality of the memory state to generate a condensed memory state; and modifying, based on a last memory state and a last condensed memory state generated during a last iteration of the applying, one or more weights associated with the memory neural network; wherein after the applying and modifying, application of a subsequent free form clinical note associated with a subsequent patient across the memory neural network generates output indicative of one or more predicted diagnoses associated with the patient.

In various embodiments, each of the plurality of free form clinical notes of the training data is labeled with one or more diagnoses. In various embodiments, reducing the dimensionality includes concatenating data generated from a previous memory state associated with the memory neural network with a current condensed memory state. In various embodiments, reducing the dimensionality condenses the memory state to some fraction of its original dimension, including but not limited to half its original dimension. In various embodiments, reducing the dimensionality includes computing a weighted average of all previous memory states. In various embodiments, generating the memory state associated with the memory neural network comprises applying a previous memory state as input across a multi-layer feed-forward neural network with a sigmoid output layer to generate, as output, a weighted sum of memory slots.

In another aspect, a method for using a trained memory neural network may include: applying a given free form clinical note associated with a given patient as input across a trained memory neural network to generate output, wherein the memory neural network model is trained using the following operations: applying, as training data, a plurality of free form clinical notes and a plurality of clinical reference documents as input across the memory neural network, wherein the applying includes, for each instance of the training data, multiple iterations, wherein each of the plurality of free form clinical notes includes one or more clinical observations about a patient in textual form, and wherein each clinical reference document describes one or more diagnoses and one or more associated expected clinical observations; for each iteration of the applying: generating a memory state associated with the memory neural network, and reducing a dimensionality of the memory state to generate a condensed memory state; modifying, based on a last memory state and a last condensed memory state generated during a last iteration of the applying, one or more weights associated with the memory neural network; predicting, based on the output, one or more diagnoses associated with the patient; and providing output at one or more output devices, wherein the output is indicative of one or more of the predicted diagnoses.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

FIG. 5 depicts an example method for practicing selected aspects of the present disclosure.

FIG. 6 depicts another example method for practicing selected aspects of the present disclosure.

DETAILED DESCRIPTION

Diagnosis of a clinical condition is a challenging task, which often requires significant medical investigation. The cognitive burden of dealing with complex patient situations could be reduced by automatically generating and providing suggestions to physicians of the most probable diagnostic options for optimal clinical decision-making. Free form clinical notes recorded in, for instance, an EHR, often may contain pertinent information that is useful to predict diagnoses and/or outcomes. It would be beneficial to be able to automatically predict outcomes and/or diagnoses using free form clinical notes, in addition to or instead of the other data points described above. However, the conventional models described above are not well-suited for such a tasks, e.g., because they are not sufficiently scalable.

Accordingly, techniques are described herein for training and applying "condensed memory networks," or "C-MemNNs." C-MemNNs may be designed to efficiently store condensed representations in memory, thereby maximizing the utility of limited memory slots. In various embodiments, a condensed form of a memory state which contains some information from earlier iterations or hops may, in effect, "learn" efficient representation. For example, in some embodiments, a simpler form of knowledge retention from previous iterations may be achieved by taking a weighted average of memory states from all the iterations, in which will be referred to herein as an "average MemNN," or "A-MemNN." While examples described herein relate to predicting outcomes and/or diagnoses based on free form clinical notes (e.g., EHRs), this is not meant to be limiting. Techniques described herein may be used in a variety of other contexts. For example, techniques described herein could be used, for instance, to predict outcomes based on, and/or extract information from, legal documents. Additionally or alternatively, techniques described herein could be used to predict/estimate attributes of people and/or other entities (e.g., locations, companies, organizations, etc.) based on knowledge bases such as surveys, user reviews, feedback, etc. As another example, criminal histories and/or police files may be analyzed using techniques described herein to, for instance, predict recidivism.

Figure 1:
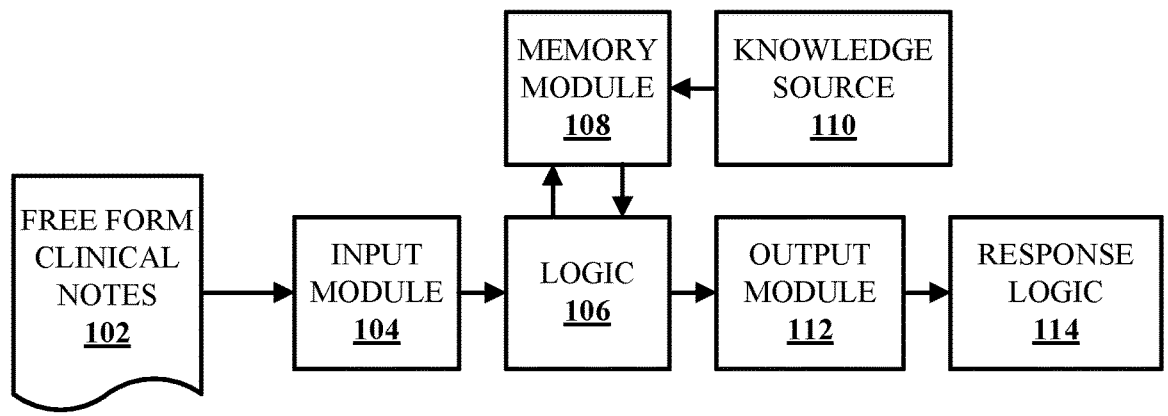
FIG. 1 schematically illustrates an example architecture and process flow that may be utilized in various embodiments described herein.

FIG. 1 schematically depicts one example of architecture and process flow that may be employed to build and apply C-MemNNs (and/or A-MemNNs) to make predictions. In FIG. 1, one or more free form clinical notes 102, such as notes taken by a clinician in an EHR, may be provided as input to an input module 104. Input module 104 may be configured to convert these notes into various forms (described in more detail below) that are then provided to a logic 106. Logic 106 may take the form of one or more field-programmable gate arrays ("FPGAs"), one or more application-specific integrated circuits ("ASICs"), and/or one or more microprocessors that execute instructions in physical memory (not depicted in FIG. 1) to implement one or more components depicted in FIG. 1, such as input module 104. The various components depicted in FIG. 1 and elsewhere in the figures may be implemented using any combination of hardware or software.

Logic 106 may read data from, and write data to, a memory module 108. As noted above, memory module 108 may be the component that manages the memory associated with the C-MemNN. Thus, while memory module 108 may utilize physical memory (e.g., RAM, ROM, flash memory, etc.) to store data, at a higher level, memory module 108 (which again may be implemented using any combination of hardware or software) may be configured to manage the logical memory associated with the C-MemNN. In various embodiments, memory module 108 may include memory slots which may or may not be accessible using hashes. These memory slots may be populated, for instance, with information from a knowledge source 110.

In various embodiments, knowledge source 110 may include a corpus of documents that include information pertinent to the task at hand. These documents may be used to train one or more machine learning models (e.g., neural networks) and to populate memory slots of memory module 108. For example, in some embodiments, knowledge source 110 may include individual documents that include a title that indicates one or more diagnoses, and content that describes various attributes of (e.g., are indicative of) the diagnosis, such as symptoms, vital signs, clinical observations, treatments, etc. For purposes of the examples described herein, knowledge source 110 may include individual documents (i.e. document content) and titles that will be referred to, respectively, as $(k_1, v_1), (k_2, v_2), \ldots (k_m, v_{ml})$, where k refers to key and v refers to value based on the key-value memory network literature. The titles $v_{1-m}$ of these individual documents will also be referred to as the diagnoses, y.

Memory module 108 may organize its internal memory into slots, $m_1, m_2, \ldots, m_r$. In various embodiments, for a given input text (e.g., free form clinical notes) $x_1, x_2, x_n$, and the knowledge source, organized in a key-value form $(k_1, v_1), (k_2, v_2), \ldots (k_m, v_m)$, logic 106 may learn one or more functions F, such as C-MemNNs, such that:

$$F(x_n, \{k_m, V_m\}) = \hat{y} \rightarrow y \qquad (1)$$

Figure 2:
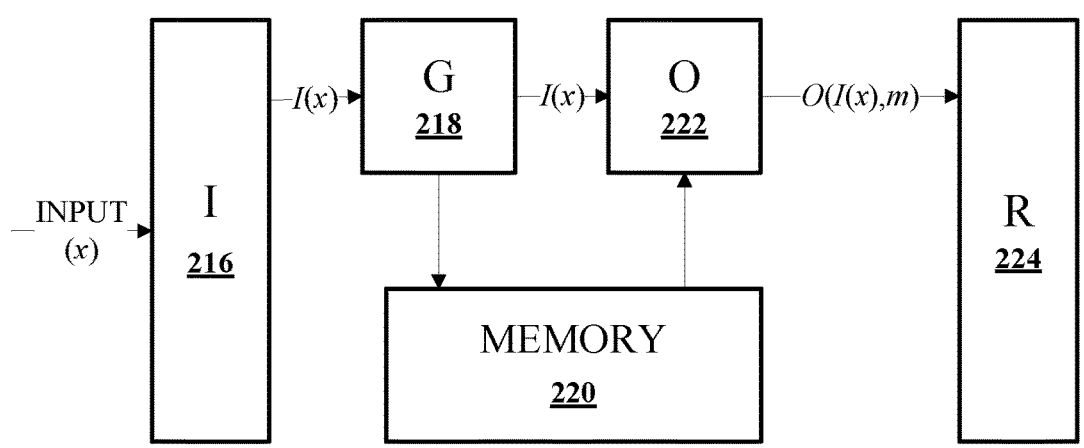
FIG. 2 schematically depicts example logical components of a memory neural network that may be employed in various embodiments described herein.

The function F may be broken down into four parts: Input, Generalization, Output, and Response. Referring to FIG. 2, which schematically depicts components of a conventional MemNN, in some embodiments, at an input component 216 (which may be implemented in some cases at input module 104), input x may be converted (or "embedded") to some internal memory state (I(x) in FIG. 2, u elsewhere herein), e.g., a feature space embedding, using learned weights, which will be referred to herein as B. These embeddings may be learned using various techniques, such as bag of words ("BOW"), gated recurrent units ("GRUs"), Long Short Term Memory ("LSTM"), and/or pre-trained vectors such as global vectors for word representation ("GloVe") and/or Word2Vec. The internal memory state u is somewhat similar to the hidden state of recurrent neural networks ("RNN").

Generalization component 218 may be configured to update memory 220 based on its internal memory state, u. In some embodiments, generalization component 218 may be implemented as part of memory module 108, such that it writes initial data to a memory 220 associated with the C-MemNN and updates the memory slots as needed. Conventional MemNNs update all slots in memory. However, this is not feasible when the size of knowledge source 110 is large, as is the case when knowledge source 110 includes myriad clinical individual documents covering a wide range of diagnoses. Accordingly, and as will be described below, memory 220 may be organized into key-value pairs and hashing may be used during each iteration of application of the C-MemNN to retrieve a relatively small portion of keys for a given input x.

Output component 222 may be configured to generate a so-called "output state" or "output memory representation" O(I(x), m). In various embodiments, this output state may include a combination of preexisting memory state u and input x. In some embodiments, the output memory representation may be the transformation of knowledge (k, v) to some internal representation, m and c, respectively. In some embodiments, a two-step process may be used as two different learned spaces may be formed using the knowledge source documents titles and content. Thus, a first matrix A may be leaned to transform content (keys) and a second matrix C may be learned to transform titles (values). Let k represent the hop or iteration number. The output memory representation produced by output 222 may be obtained using the following equation:

$$o^k = \Sigma_i \text{Addressing}(u^k, m_i^k) \cdot c_i^k \qquad (2)$$

Addressing may be a function that takes a current memory state u as input and provides a relevant memory representation m.

Response component 224 may be configured to convert the output O(I(x), m), or more simply, the internal memory state u (which as noted above is updated at each iteration), into a response that is desired from the model. In many examples described herein, the desired response may be, for instance, one or more predictions of one or more outcomes and/or diagnoses. In addition, in some embodiments, response component 224 may combine the latest internal memory state u, a condensed memory state ũ (described in more detail below), and the latest output representation o to generate a predicted label ŷ (e.g., one or more predicted diagnoses).

Figure 3:
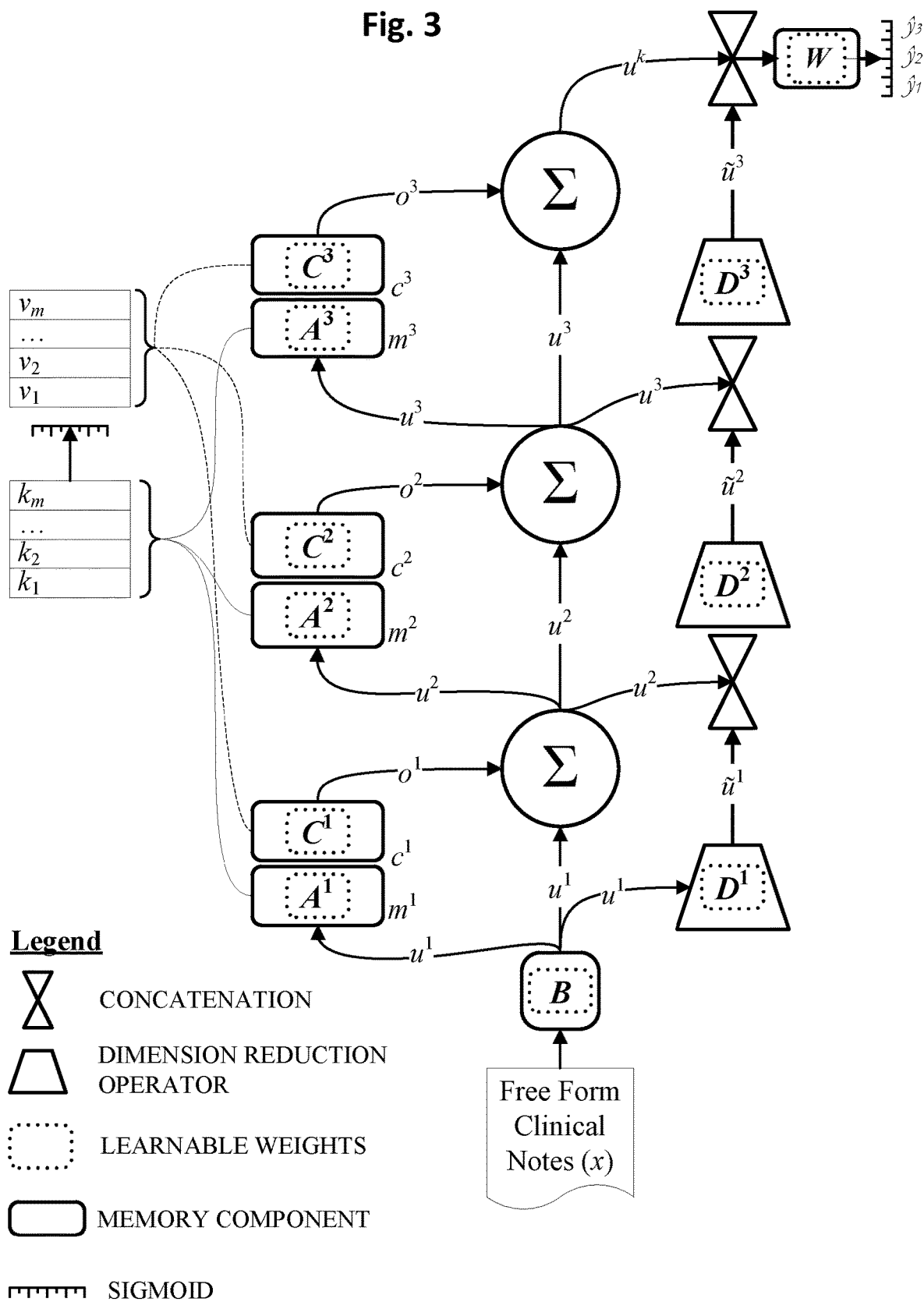
FIG. 3 schematically depicts one example of how memory of a condensed memory neural network configured with selected aspects of the present disclosure may be transformed over multiple iterations or hops.

FIG. 3 schematically depicts one example of how memory of a C-MemNN or A-MemNN may be transformed over multiple iterations or hops, e.g., as part of training the C-MemNN or A-MemNN. As noted above, the input x may take the form of free form clinical notes (e.g., EHRs) shown at bottom. As part of the function performed by input component 216 of FIG. 2, the free form clinical notes, or x, are converted to some internal representation of a first memory state $u^1$ using learned weights B. This first memory state $u^1$ may be provided (e.g., in parallel) to memory module 108 during a first iteration or hop. Memory module 108 may transform $u^1$ to internal representations $m^1$ and $c^1$, e.g., by way of the aforementioned matrices $A^1$ and $C^1$. For example, in some embodiments, the first memory state $u^1$ may be combined with memory key slots $m^1$ using transformation matrix $A^1$. Memory addressing may then be used to retrieve the corresponding memory value $c^1$ (which may be a title or diagnosis). This value may be transformed, e.g., using transformation matrix $C^1$, to output memory representation $o^1$.

Figure 4:
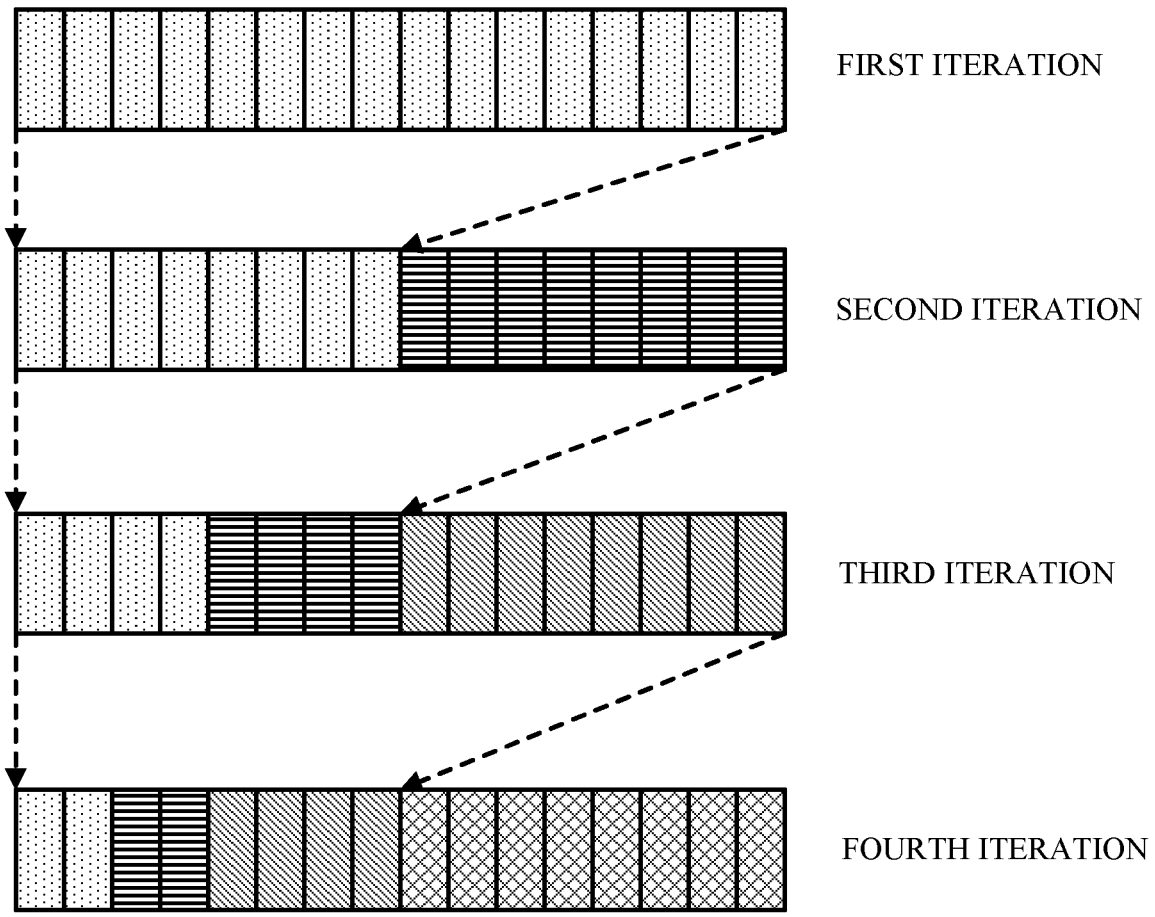
FIG. 4 schematically depicts condensation of memory.

Meanwhile, also during the first iteration, $u^1$ may be condensed to some smaller dimension, such as half its original dimension (or one third, one fourth, or any other reduced dimension), using a transformation matrix $D^1$. For example, if $u^1$ is of size 1×K, then transformation matrix $D^1$ may be of size K×K/2. The result of the dimensionality reduction will be referred to herein as first condensed memory state $ũ^1$. This is the end of the first iteration. The process may then be repeated for a desired number of iterations, such as the three iterations depicted in FIG. 3. After each iteration r, the condensed memory state it becomes the concatenation of its previous state and its current state, each reduced to some fraction (e.g., half) of its original dimension. An example of this is depicted in FIG. 4, in which the shaded regions represent, respectively, condensed memory state ũ at each of four iterations. As can be seen in FIG. 4, during each iteration, the previous state of ũ is condensed (e.g., dimensionality reduced) to half its original size.

Referring back to FIGS. 2 and 3, response component 224 may combine the last memory state u generated during the last iteration, the last condensed memory state ũ generated during the last iteration, and the last output representation o generated during the last iteration, to provide one or more predicted labels ŷ, which in the clinical note context may correspond to predicted diagnoses and/or outcomes. In some embodiments, u and o generated during the last iteration may be summed, and a dot product of the sum may be taken, e.g., using another learned transformation matrix W. This value may then be concatenated with the condensed memory state ũ generated during the last iteration, and this value may be passed through a sigmoid function to obtain a likelihood of each predicted label ŷ. In some embodiments, sigmoid is used instead of, for instance, softmax, in order to obtain multiple predicted labels $\hat{y}_1, \ldots, \hat{y}_r$ among R possible labels. For instance, the following equations may be used in various embodiments:

$$u^{k+1} = u^k + o^k \quad (3)$$

$$\tilde{u}^{k+1} = u^{k+1} \oplus D_1 \cdot \tilde{u}^k \quad (4)$$

In equation (4), the ⊕ symbol denotes concatenation. In other words, the condensed memory state ũ is used in combination with the conventional memory state u to make an inference. In some embodiments, and as was depicted in FIG. 4, ũ may be transformed to include the information of previous iterations, but in lower dimensional feature space. This enables a longer term memory representation that is better able to represent hierarchy in memory than the conventional networks described in the background. In some embodiments, a prediction for a particular label or class (e.g., particular diagnosis or outcome) can be computed using an equation such as the following:

$$\hat{y}_r = \underset{r \in R}{\operatorname{argmax}} \frac{1}{1 + e^{-1*(\tilde{u}^{k+1} \cdot W)}} \quad (5)$$

As noted above, C-MemNNs described herein transform ũ at each iteration using, for instance, equation (4) above. In other words, previous values of u are taken into account along with present value of u when determining ũ, and in some cases the present value of u may be weighted more heavily. However, this is not meant to be limiting. Other techniques may be used to calculate ũ. For example, to avoid addition of more learned parameters to the model, in some embodiments, an Average MemNN, or "A-MemNN," may be used instead. In an A-MemNN, memory hierarchy may be captured in memory representation without adding learned parameters. For example, in some embodiments, a weighted average of the condensed memory state ũ may be computed across multiple iterations. Instead of concatenating condensed memory states ũ from previous iterations, an exponential moving average may be maintained from multiple iterations, e.g., using an equation such as the following:

$$\tilde{u}^{k+1} = \tilde{u}^k + \frac{\tilde{u}^{k-1}}{2} + \frac{\tilde{u}^{k-2}}{4} + \cdots \quad (6)$$

In some such embodiments, the starting condensememory state ũ¹ may be equivalent to the initial memory state u¹.

Key-value addressing as used with KV-MemNN uses softmax on the product of question embeddings and retrieves keys to learn a relevance probability distribution over memory slots for a simple factoid question answering task. The representation obtained is then the sum of the output memory representation o, weighted by those probability values. KV-MemNN was designed to pick the single most relevant answer given a set of candidate answers. The use of softmax significantly decreases the estimated relevance of all but the most probable memory slot. This presents a problem for multi-label classification in which several memory slots may be relevant for different target labels, as a single clinical note may evidence multiple diagnoses and/or outcomes. While changing softmax to sigmoid may help to balance the feature representation across different labels (e.g., diagnoses), it is not a solution for representing dense representation of the memory. In other words, sigmoid helps in independent scaling, and the condensed state ũ helps for hierarchical representation.

Accordingly, in various embodiments, a different addressing scheme, referred to herein as "gated addressing," may be employed. Gated addressing uses a multi-layer feed-forward neural network ("FNN") with a sigmoid output layer to determine the appropriate weights for each memory slot. The FNN may output a weight value between 0 and 1 for each memory slot, and a weighted sum of memory slots may be obtained.

The learned values or weights (e.g., A, B, C, D, and/or W in FIG. 3) may be learned using various techniques. In some embodiments, stochastic gradient descent may be employed to optimize the weights. The learning rate determines how quickly or slowly the model should update the parameters in order to minimize the loss function of the network. A quick progression towards the target may lead to avoiding the global minima whereas a slow progression may lead to a longer training time. Thus, it is beneficial to obtain a balanced strategy for learning rate selection. For a large training data size, batch learning has shown to be effective in managing the computational complexity as well as reaching the convergence in an optimal manner by avoiding local minima or saddle points. Thus, the learning rate and the batch size of the model may be set based on heuristics, observations or experiments. A random search optimization algorithm or other known optimization strategies may be used to find the most appropriate values for such hyperparameters like learning rate and batch size.

For the final prediction layer, a fully connected layer may be used on top of the output from equation (5) with a sigmoid activation function. The loss function may be the sum of cross entropy from prediction labels and prediction memory slots using addressing schema. In some experiments, complexity of the model may be penalized by adding L2 regularization to the cross entropy loss function. Dropout with probability of 0.5 may be used in some embodiments on the output-to-decision sigmoid layer, and the norm of the gradients may be limited, e.g., to be below 20. Such regularization and dropout mechanisms would ensure that the model does not suffer from overfitting the training data, which would lead to higher testing set accuracy. Models may be trained on, for instance, 80% of the data and validated on 10%. The remaining 10% may be used as a test set which is evaluated only once across all experiments with different models. More generally, the learned weights may be learned by applying, as input across one or more memory neural networks, labeled free form clinical notes (e.g., the labels may be actual diagnoses), and individual documents that include a title that indicates one or more diagnoses, and content that describes various attributes of (e.g., are indicative of) the diagnosis, such as symptoms, vital signs, clinical observations, treatments, etc. Error between output of the memory neural network(s) and the labels assigned to the input free form clinical notes may be corrected, e.g., using the various optimization techniques described above (e.g., stochastic gradient descent) to train the various learned weights.

FIG. 5 depicts an example method 500 for training a memory neural network in accordance with selected aspects of the present disclosure, in accordance with various embodiments. For convenience, the operations of the flow chart are described with reference to a system that performs the operations. This system may include various components of various computer systems, including 700. Moreover, while operations of method 500 are shown in a particular order, this is not meant to be limiting. One or more operations may be reordered, omitted or added.

At block 502, a corpus free form clinical notes (which may or may not be labeled) and a corpus of clinical reference documents may, as training data, be applied as input across a trained C-MemNN configured with selected aspects of the present disclosure. As noted above, each clinical note may include one or more clinical observations about a patient, such as observes signs/symptoms, treatments, lab results, etc. In various embodiments, the applying may include, for each instance of the training data, multiple iterations, such as a maximum number of iterations (which may be selected manually, based on a length of the free form clinical note, etc.). For example, at block 504, a determination may be made of whether the maximum number of iterations has been reached. If the answer is no, the C-MemNN model learns from the free form clinical note iteratively. For example, at block 506, a memory state $u^i$ (i is the current iteration) associated with the C-MemNN may be generated.

At block 508, a dimensionality of the memory state $u^i$ may be reduced to generate a condensed memory state $\tilde{u}^i$. In some embodiments, reducing the dimensionality may include concatenating data generated from a previous memory state $u^{i-1}$ associated with the memory neural network with a current condensed memory state $u^i$. In some embodiments, the data generated from the previous memory state $u^{i-1}$ may include a sum of a previous memory state and an output memory representation $o^i$. In other embodiments, reducing the dimensionality may include computing a weighted average of all previous memory states, as described above with respect to equation (6). Blocks 504-508 may be repeated until the maximum number of iterations is reached.

If the answer at block 504 is yes, then method 500 may proceed to block 510. At block 510, the system may modify, e.g., based on a last memory state $u^i$ and a last condensed memory state $\tilde{u}^i$ generated during a last iteration of the applying, one or more weights associated with the C-MemNN, such as A, B, C, D, and/or W. It should be understood that these weights may be modified during each iteration; hence, the iterating superscript numbers depicted in association with each transformation matrix in FIG. 3. Once the C-MemNN (or A-MemNN) is trained using method 500 (i.e. after the applying and modifying), application of a subsequent free form clinical note associated with a subsequent patient across the C-MemNN or A-MemNN generates output indicative of one or more predicted diagnoses associated with the patient.

FIG. 6 depicts an example method 600 of applying a trained memory neural network in accordance with selected aspects of the present disclosure, in accordance with various embodiments. For convenience, the operations of the flow chart are described with reference to a system that performs the operations. This system may include various components of various computer systems, including 700. Moreover, while operations of method 600 are shown in a particular order, this is not meant to be limiting. One or more operations may be reordered, omitted or added.

At block 602, the system may train the memory neural network (e.g., C-MemNN or A-MemNN) using, as training data, free form clinical notes (which may or may not be labeled with diagnoses) and clinical reference documents, as described above with respect to FIG. 5. In some embodiments, the operations of block 602 may be identical to the operations of method 500.

At block 604, the system may apply a given free form clinical note associated with a given patient as input across the trained memory neural network to generate output. At block 606, the system may predict, e.g., based on the output generated at block 604, one or more diagnoses or outcomes of the given patent.

At block 608, the system may provide output at one or more output devices. The output may be indicative of one or more of the predicted diagnoses. For example, in some embodiments, one or more predicted diagnoses (or outcomes) may be presented on a display device or on a report printed to paper. In some embodiments, one or more of the presented predicted diagnoses may include a probability that is determined based on the sigmoid function described previously. In some embodiments, if the probability of a particular diagnosis satisfies a threshold, it may be presented more conspicuously than other diagnoses (e.g., bolded, in larger text, different color, etc.), and/or may trigger an alarm if the predicted diagnosis requires immediate attention. In some embodiments, the predicted diagnosis may be determined automatically, e.g., in response to a clinician filing an EHR in a hospital information system. In some such embodiments, the clinician may be informed of the predicted diagnoses on a display device, e.g., immediately or sometime later, e.g., through an email or other message means.

Figure 7:
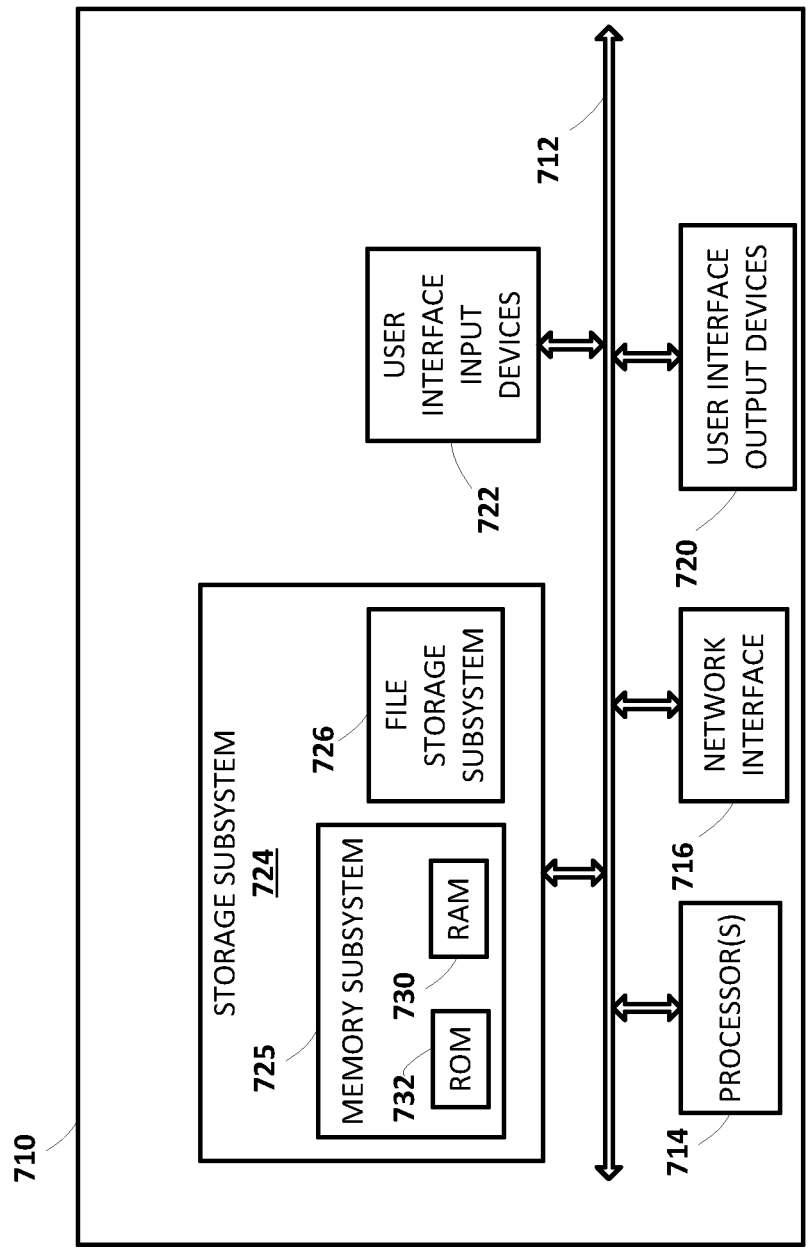
FIG. 7 schematically depicts an example computer architecture.

FIG. 7 is a block diagram of an example computer system 710. Computer system 710 typically includes at least one processor 714 which communicates with a number of peripheral devices via bus subsystem 712. As used herein, the term "processor" will be understood to encompass various devices capable of performing the various functionalities attributed to components described herein such as, for example, microprocessors, GPUs, FPGAs, ASICs, other similar devices, and combinations thereof. These peripheral devices may include a data retention subsystem 724, including, for example, a memory subsystem 725 and a file storage subsystem 726, user interface output devices 720, user interface input devices 722, and a network interface subsystem 716. The input and output devices allow user interaction with computer system 710. Network interface subsystem 716 provides an interface to outside networks and is coupled to corresponding interface devices in other computer systems.

User interface input devices 722 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 710 or onto a communication network.

User interface output devices 720 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 710 to the user or to another machine or computer system.

Data retention system 724 stores programming and data constructs that provide the functionality of some or all of the modules described herein. For example, the data retention system 724 may include the logic to perform selected aspects of FIGS. 1-4, as well as to implement selected aspects of method 500 and/or method 600.

These software modules are generally executed by processor 714 alone or in combination with other processors. Memory 725 used in the storage subsystem can include a number of memories including a main random access memory (RAM) 730 for storage of instructions and data during program execution, a read only memory (ROM) 732 in which fixed instructions are stored, and other types of memories such as instruction/data caches (which may additionally or alternatively be integral with at least one processor 714). A file storage subsystem 726 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 726 in the data retention system 724, or in other machines accessible by the processor(s) 714. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 712 provides a mechanism for letting the various components and subsystems of computer system 710 communicate with each other as intended. Although bus subsystem 712 is shown schematically as a single bus, alternative implementations of the bus subsystem may use multiple busses. In some embodiments, particularly where computer system 710 comprises multiple individual computing devices connected via one or more networks, one or more busses could be added and/or replaced with wired or wireless networking connections.

Computer system 710 can be of varying types including a workstation, server, computing cluster, blade server, server farm, or any other data processing system or computing device. In some embodiments, computer system 710 may be implemented within a cloud computing environment. Due to the ever-changing nature of computers and networks, the description of computer system 710 depicted in FIG. 7 is intended only as a specific example for purposes of illustrating some implementations. Many other configurations of computer system 710 are possible having more or fewer components than the computer system depicted in FIG. 7.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method for training a memory neural network implemented by one or more processors, comprising:
   applying, as training data, a plurality of free form clinical notes and a plurality of clinical reference documents as input across the memory neural network, wherein the applying includes multiple iterations for each instance of the training data, wherein each of the plurality of free form clinical notes includes one or more clinical observations about a patient in textual form, and wherein each clinical reference document describes one or more diagnoses and one or more associated expected clinical observations;
   for each iteration of the applying:
     generating a memory state using previous learned weights associated with the memory neural network, wherein the memory state is transformed into an output representation using a first transformation matrix and performing a summation operation between the memory state and the output representation to generate a current memory state, and reducing a dimensionality of the memory state to generate a condensed memory state in parallel with the generation of the current memory state;
     generating a current condensed memory state by concatenating the current memory state and condensed memory state, the condensed memory state comprising the memory state that has been reduced in dimensionality before the concatenating operation, by applying a second transformation matrix to the memory state to generate a weighted average of the memory state, the second transformation matrix corresponding in dimensionality to an intended scale of the reduction of dimensionality; and
   generating a last memory state and a last condensed memory state, wherein the last memory state comprises the current memory states from at least a portion of previous iterations, and wherein the last condensed memory state comprises the current condensed memory state from at least a portion of the previous iterations;
   combining the last memory state, and the last condensed memory state to provide one or more predicted labels;
   modifying, based on the last memory state and the last condensed memory state generated during a last iteration of the applying and the predicted labels, one or more weights associated with the memory neural network, wherein a portion of the one or more weights is further associated with generating the memory state;
   wherein after the applying and modifying, application of a subsequent free form clinical note associated with a subsequent patient across the memory neural network generates output indicative of one or more predicted diagnoses associated with the patient.

2. The method of claim 1, wherein each of the plurality of free form clinical notes of the training data is labeled with one or more diagnoses.

3. The method of claim 1, wherein reducing the dimensionality condenses the memory state to half of its original dimension.

4. The method of claim 1, wherein reducing the dimensionality includes computing a weighted average of all previous memory states.

5. The method of claim 1, wherein generating the memory state associated with the memory neural network comprises applying a previous memory state as input across a multi-layer feed-forward neural network with a sigmoid output layer to generate, as output, a weighted sum of memory slots.

6. At least one non-transitory computer-readable medium comprising instructions that, in response to execution of the instructions by one or more processors, cause the one or more processors to perform the following operations:
   applying a given free form clinical note associated with a given patient as input across a trained memory neural network to generate output, wherein the memory neural network is trained using the following operations:
     applying, as training data, a plurality of free form clinical notes and a plurality of clinical reference documents as input across the memory neural network, wherein the applying includes, for each instance of the training data, multiple iterations, wherein each of the plurality of free form clinical notes includes one or more clinical observations about a patient in textual form, and wherein each clinical reference document describes one or more diagnoses and one or more associated expected clinical observations;
   for each iteration of the applying:
   generating a memory state using previous learned weights associated with the memory neural network, wherein the memory state is transformed into an output representation using a first transformation matrix and performing a summation operation between the memory state and the output representation to generate a current memory state, and reducing a dimensionality of the memory state to generate a condensed memory state in parallel with the generation of the current memory state;

generating a current condensed memory state by concatenating the current memory state and condensed memory state, the condensed memory state comprising the memory state that has been reduced in dimensionality before the concatenating operation, by applying a second transformation matrix to the memory state to generate a weighted average of the memory state, the second transformation matrix corresponding in dimensionality to an intended scale of the reduction of dimensionality; and generating a last memory state and a last condensed memory state, wherein the last memory state comprises the current memory states from at least a portion of previous iterations, and wherein the last condensed memory state comprises the current condensed memory state from at least a portion of the previous iterations;

combining the last memory state, and the last condensed memory state to provide one or more predicted labels;

modifying, based on the last memory state and the last condensed memory state generated during a last iteration of the applying and the predicted labels, one or more weights associated with the memory neural network, wherein a portion of the one or more weights is further associated with generating the memory state;

predicting, based on the output, one or more diagnoses associated with the patient; and providing output at one or more output devices, wherein the output is indicative of one or more of the predicted diagnoses.

7. The non-transitory computer-readable medium of claim 6, wherein each of the plurality of free form clinical notes of the training data is labeled with one or more diagnoses.

8. The non-transitory computer-readable medium of claim 6, wherein the data generated from the previous memory state includes a sum of a previous memory state and an output memory representation.

9. The non-transitory computer-readable medium of claim 6, wherein reducing the dimensionality includes computing a weighted average of all previous memory states.

10. The non-transitory computer-readable medium of claim 6, wherein generating the memory state associated with the memory neural network comprises applying a previous memory state as input across a multi-layer feed-forward neural network with a sigmoid output layer to generate, as output, a weighted sum of memory slots.

11. The non-transitory computer-readable medium of claim 6, wherein providing output comprises presenting one predicted diagnosis more conspicuously than others based on a probability associated with the one predicted diagnosis.

12. A system comprising one or more processors and memory operably coupled with the one or more processors, wherein the memory stores instructions that, in response to execution of the instructions by one or more processors, cause the one or more processors to perform the following operations:

applying, as training data, a plurality of free form clinical notes and a plurality of clinical reference documents as input across a memory neural network, wherein the applying includes multiple iterations for each instance of the training data, wherein each of the plurality of free form clinical notes includes one or more clinical observations about a patient in textual form, and wherein each clinical reference document describes one or more diagnoses and one or more associated expected clinical observations;

for each iteration of the applying:

generating a memory state using previous learned weights associated with the memory neural network, wherein the memory state is transformed into an output representation using a first transformation matrix and performing a summation operation between the memory state and the output representation to generate a current memory state, and reducing a dimensionality of the memory state to generate a condensed memory state in parallel with the generation of the current memory state;

generating a current condensed memory state by concatenating the current memory state and condensed memory state, the condensed memory state comprising the preceding memory state that has been reduced in dimensionality before the concatenating operation, by applying a second transformation matrix to the memory state to generate a weighted average of the memory state, the second transformation matrix corresponding in dimensionality to an intended scale of the reduction of dimensionality; and generating a last memory state and a last condensed memory state, wherein the last memory state comprises the current memory states from at least a portion of previous iterations, and wherein the last condensed memory state comprises the current condensed memory state from at least a portion of the previous iterations;

combining the last memory state, and the last condensed memory state to provide one or more predicted labels;

modifying, based on the last memory state and the last condensed memory state generated during a last iteration of the applying and the predicted labels, one or more weights associated with the memory neural network, wherein a portion of the one or more weights is further associated with generating the memory state;

wherein after the applying and modifying, application of a subsequent free form clinical note associated with a subsequent patient across the memory neural network generates output indicative of one or more predicted diagnoses associated with the patient.

13. The system of claim 12, wherein each of the plurality of free form clinical notes of the training data is labeled with one or more diagnoses.

14. The system of claim 12, wherein the data generated from the current memory state includes a sum of a previous memory state and an output memory representation.

15. The system of claim 12, wherein reducing the dimensionality includes computing a weighted average of all previous memory states.

16. The system of claim 12, wherein generating the memory state associated with the memory neural network comprises applying a previous memory state as input across another neural network to generate, as output, a weighted sum of memory slots.

17. The system of claim 16, wherein the another neural network comprises a feed-forward neural network.

* * * * *